(12) United States Patent
Lenarz et al.

(10) Patent No.: US 8,518,112 B2
(45) Date of Patent: Aug. 27, 2013

(54) DEVICE FOR VARIABLE-LENGTH FIXING OF THE ACTUATOR END PIECE OF AN ACTIVE HEARING IMPLANT IN THE MIDDLE EAR

(75) Inventors: Thomas Lenarz, Hannover (DE); Uwe Steinhardt, Hirrlingen (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 64 days.

(21) Appl. No.: 13/238,626

(22) Filed: Sep. 21, 2011

(65) Prior Publication Data
US 2012/0078368 A1 Mar. 29, 2012

(30) Foreign Application Priority Data
Sep. 24, 2010 (DE) .......................... 10 2010 046 457

(51) Int. Cl.
*A61F 2/18* (2006.01)
(52) U.S. Cl.
USPC ............................................................ 623/10
(58) Field of Classification Search
USPC .............................................. 623/10; 600/25
See application file for complete search history.

(56) References Cited

U.S. PATENT DOCUMENTS

| 5,935,167 A | 8/1999 | Awengen |
| 5,941,814 A | 8/1999 | Lehner et al. |
| 6,554,861 B2 | 4/2003 | Knox et al. |
| 6,579,317 B2 | 6/2003 | Kurz |
| 6,830,587 B2 * | 12/2004 | a Wengen et al. ............... 623/10 |
| 7,204,850 B2 * | 4/2007 | Steinhardt et al. ............... 623/10 |
| 7,628,812 B2 | 12/2009 | Awengen |
| 2008/0208338 A1 | 8/2008 | Steinhardt et al. |
| 2009/0164010 A1 * | 6/2009 | Steinhardt et al. ............... 623/10 |
| 2010/0262236 A1 | 10/2010 | Steinhardt et al. |
| 2010/0280544 A1 * | 11/2010 | Banks ........................... 606/210 |

FOREIGN PATENT DOCUMENTS

| DE | 200 14 659 | 11/2000 |
| DE | 20 2005 011 485 | 11/2005 |
| DE | 10 2005 027 215 | 12/2006 |
| DE | 10 2009 016 468 | 12/2009 |
| EP | 1 181 907 | 2/2002 |
| WO | 02/069850 | 9/2002 |

* cited by examiner

*Primary Examiner* — David Isabella
*Assistant Examiner* — Dinah Baria
(74) *Attorney, Agent, or Firm* — Michael J. Striker (57) ABSTRACT

A device for adjusting and fixing relative position between an actuator end piece of an active hearing implant and an element of the ossicular chain or a coupling part to the human inner ear has a connecting element with a first coupling element for coupling to the actuator end piece, a second coupling element, and a shaft-shaped middle part, and the first coupling element geometrically encompasses the actuator end piece with two opposing parallel arms each having a pattern element to fix the encompassed actuator end piece in selectable discrete axial positions in a direction parallel to an axis of the shaft-shaped middle part, for variable-length adaptation and fixing of the actuator end piece relative to the first coupling element in a direction transverse to the axis.

18 Claims, 11 Drawing Sheets

DEVICE FOR VARIABLE-LENGTH FIXING OF THE ACTUATOR END PIECE OF AN ACTIVE HEARING IMPLANT IN THE MIDDLE EAR

CROSS-REFERENCE TO RELATED APPLICATION

The invention described and claimed hereinbelow is also described in German Patent Application DE 2010 046 457.0 filed on Sep. 24, 2010. This German Patent Application, whose subject matter is incorporated here by reference, provides the basis for a claim of priority of invention under 35 U.S.C. 119(a)-(d).

BACKGROUND OF THE INVENTION

The invention relates to a device for adjusting and fixing the relative position between an actuator end piece of an active hearing implant on the one hand and on the other hand, an element of the ossicular chain or a coupling part to the human inner ear, in particular to the perilymph of the labyrinth system or to the endolymphatic compartment; the device is equipped with a connecting element having a first coupling element for coupling the connecting element to the actuator end piece, having a second coupling element for coupling the connecting element to the incus, the stapes, the stapes footplate, the oval window, or the round window of the human middle ear, and having a shaft-shaped middle part between the first coupling element and the second coupling element.

Such a device for adjusting and fixing the relative position of two elements of an active hearing implant is known from U.S. Pat. No. 5,941,814.

In the event of partially or entirely missing or damaged ossicles of the human middle ear, hearing implants are used to transmit the sound, which strikes the outer ear, or a corresponding audio signal to the inner ear. In this context, a distinction is drawn between passive ossicular prostheses on the one hand that physically replace parts of the ossicular chain, with the transmission of sound occurring "passively," i.e. without assistance from electronic aids, and active hearing implants on the other hand that receive electrical signals, which correspond to the audio signals, from an electronic amplifier of a hearing aid worn outside the middle ear, transmitted via an actuator implanted in the middle ear, convert them through mechanical motion back into acoustic oscillations and transmit them from a vibrating actuator end piece into the inner ear via a suitable connecting element. Such active hearing implants—and in particular, the problem of an optimal acoustic coupling of the actuator end piece to the inner ear—are the subject of the present invention.

The diameter of the generally cylindrical actuator end piece is usually standardized, i.e. is always the same size or is at least provided in a group of particular discrete sizes from which a selection is made in association with the different individual circumstances of the individual patient.

DE 200 14 659 U1 has disclosed a device for adjusting and fixing the relative position between the actuator end piece ("actuator") of an active hearing implant on the one hand and an element of the human ossicular chain on the other hand. In this context, the known device is equipped with a connecting element having a first coupling element in the form of a receptacle with clamps for coupling to the actuator end piece, having a second coupling element in the form of a clip for coupling to the stapes, and having a shaft-shaped middle part between the first and second coupling elements.

In U.S. Pat. No. 5,941,814, which was cited at the beginning, as a first coupling element for coupling the connecting element to the actuator end piece, a crimping sleeve embodied in the form of a hollow cylinder is proposed, through which the actuator end piece is inserted during the implanting operation and then permanently fastened by being cold caulked with a crimping tool. Between the outside of this crimping sleeve and the shaft-shaped middle part, there is a rigid mechanical connection, for example produced by means of a spot weld or soldering point.

One problem with this known geometric arrangement is the lack of flexibility for an exact relative spatial positioning between the vibrating actuator end piece and the first coupling element of the connecting element in the middle ear. Sliding the first coupling element a greater or lesser distance into the cylindrical cavity of the crimping sleeve does in fact achieve a certain amount of variability in the direction of the cylinder axis of the crimping sleeve. However, there is no possibility whatsoever of adjusting in a direction perpendicular to this cylinder axis so that the fine three-dimensional positioning of the connecting point between the actuator end piece and the first coupling element and therefore a precise fixing of the final position of the entire device can only be carried out in an extremely imprecise fashion.

This correspondingly leads to undesirable stresses within the implant structure and therefore to less than optimal geometric adaptation of the relative positions of the individual connecting pieces, which finally in turn results in a significantly poorer frequency response of the entire hearing implant and less of an improvement in the sound conduction than the entire device with the active hearing aid is actually capable of from a technical standpoint.

SUMMARY OF THE INVENTION

In light of this, the object of the present invention is to use the simplest technical means to simply and inexpensively create a device of the generic type described at the beginning, which in addition to the adjustability in the axial direction of the actuator end piece, also permits a convenient, variable-length adaptation and fixing of the actuator end piece relative to the first coupling element in a direction transverse to the axis of the actuator end piece so that as an overall result, the acoustic oscillations in the form of sound waves produced by the actuator can be better transmitted to the parts of the hearing implant leading to the inner ear.

According to the invention, this object is attained in a way that is as surprisingly simple as it is effective in that the first coupling element is geometrically embodied so that it encompasses the actuator end piece with two opposing, essentially parallel arms and the two arms each have a pattern element, which in cooperation with the two arms, makes it possible to fix the encompassed actuator end piece in selectable discrete axial positions in a direction parallel to the shaft axis of the shaft-shaped middle part.

If the discrete axial clamping positions between the two arms are graduated finely enough, then this permits an extremely precise spatial adjustment of the coupling point between the actuator end piece and the first coupling element, which in turn also significantly improves the possibility for setting the desired spatial position of the second coupling element in the middle ear.

In one class of embodiments of the device according to the invention that is particularly preferable and relatively easy to manufacture, the pattern elements of the arms of the first coupling element, on their inner surfaces, which rest against the outer circumference of the actuator end piece in the implanted state, each have notches or indents at the respective opposite axial positions of the two arms for accommodating the actuator end piece. This makes it possible to implement a particularly precise and reproducible desired setting of the axial end position.

In an advantageous modification within this embodiment class, the notches or indents on the inner surfaces of the two arms are situated spaced equidistantly apart from one another in the axial direction, which is particularly favorable from a production standpoint.

In order to ensure a particularly favorable, durably stable fitting of the device after the setting of the desired relative end position of the actuator end piece and the first connecting element, in preferred modifications of this embodiment class, the outer circumference of the actuator end piece has projections that are geometrically embodied so that they function as counterparts that fit the notches or indents at the discrete axial positions of the pattern elements of the first coupling element.

Alternatively or in addition, in a preferred modification of this embodiment class, the outer circumference of the actuator end piece has azimuthally extending annular grooves that are geometrically embodied so that they function as counterparts that fit the notches or indents at the discrete axial positions of the pattern elements of the first coupling element. As a result, particularly when implementing a plurality of annular grooves situated one after another in the axial direction of the actuator end piece, this permits a precise positioning of the first coupling element relative to the actuator end piece in its axial direction.

Both with regard to a technical ease of manufacture and with regard to a particularly simple maneuvering, there is another preferred class of embodiments of the device according to the invention in which the first arm of the first coupling element transitions into the shaft-shaped middle part of the connecting element, the second arm is connected to the first arm via a connecting piece so that the two arms are spaced laterally apart from each other, and at the end opposite from the connecting piece, between the first arm and the free end of the second arm, an insertion region is provided for the insertion of the actuator end piece.

In modifications of this embodiment class that further improve the maneuverability, the free end of the second arm transitions into an insertion facilitating element that extends diagonally outward in a direction oriented away from the first arm and toward the outside of the second arm in order to facilitate the insertion of the actuator end piece into the insertion region of the first coupling element.

In advantageous and easy-to-manufacture modifications, the connecting piece is situated at the free end of the first coupling element oriented away from the shaft-shaped middle part.

In order to increase the inherent stability of the connecting element in the region of the first coupling element and to achieve an improved maneuverability during implantation, there are modifications of this embodiment class in which the connecting piece has two horns that each protrude laterally outward in a direction oriented away from the shaft axis of the shaft-shaped middle part.

After the hearing implant has been operatively placed in the middle ear, then the so-called "healing-in" phase begins. During this time, scars form and these generate unpredictable forces, which can often shift the prosthesis out of its local position, which has been precisely set during the operation. If the connection between the first and second coupling element is too tight, then elevated pressure peaks can also occur, which in turn can result in damage to the implant. For this reason, it is very helpful if this part of the active hearing implant has a certain degree of postoperative mobility so that in the postoperative phase, it can automatically adapt to a changed position in the edge regions. Since otherwise, the anatomical circumstances of the ear, e.g. the position, shape, and size of the stapes, the incus, the malleus, and the eardrum, it is very advantageous if hearing implants are not embodied as rigid, but instead have a certain degree of flexibility or variability.

As a rule, with the device according to the invention, the middle part between the two fastening elements is embodied in the form of an elongated shaft, as is well known from the prior art. In order to achieve the prosthesis flexibility and variability discussed above—as described in detail, for example, in EP 1 181 907 B1—in a particularly preferred class of embodiments of the device according to the invention, the connecting element can have a ball-and-socket joint that is particularly situated in the region of the shaft-shaped middle part. This gives the connecting element of certain degree of flexibility. Particularly advantageous from the standpoint of a particularly high degree of postoperative mobility of the connecting element are modifications in which the elongated shaft includes a multitude of additional rotating elements situated adjacent to one another, preferably in the form of a ball-and-socket chain. Alternatively, in a class of particularly easy-to-manufacture embodiments of the device according to the invention, the first coupling element and the shaft-shaped middle part can be embodied of one piece with each other.

In modifications of this class of simple embodiments that are particularly advantageous from a production standpoint, the connecting element is embodied of one piece with the unit comprising the first coupling element, the shaft-shaped middle part, and the second coupling element.

Possible embodiments of the invention include those in which the device or parts thereof are composed of biocompatible plastics, in particular silicone, polytetrafluoroethylene (PTFE), or polyether ether ketone (PEEK), and/or of fiber composite materials, in particular carbon fibers. In most cases, the use of these materials can prevent postoperative rejection reactions.

The device according to the invention or parts thereof can also be manufactured out of titanium and/or gold and/or tantalum and/or steel and/or an alloy of the above-mentioned metals. In particular, the material titanium, in addition to its strength and outstanding sound-conducting properties, is also known to have an excellent biocompatibility with the human middle ear.

Embodiments of the invention that are advantageous with regard to the above-mentioned postoperative position adaptation include those in which the connecting element is entirely or partially manufactured—at least in the region of the first coupling element—out of a material with shape memory properties (=memory effect) or super elastic properties, in particular a nickel/titanium alloy, preferably nitinol, which is intrinsically known, for example, from WO 02/069850 A1 or U.S. Pat. No. 6,554,861 B2, but only in connection with passive ossicular chain prostheses.

Alternatively or in addition, in other embodiments, parts of the device according to the invention can be composed of a ceramic material.

In other preferred embodiments of the device according to the invention, the second coupling element is embodied in the form of a piston or ball for coupling to the inner ear, a clip or a bell for coupling to the stapes head, a receiving part for an Ω-shaped artificial stapes footplate, a die for coupling to the natural stapes footplate, a clamp for coupling to the incus process, or a pin for coupling to the incus body. Various possibilities for embodying the second coupling element in the form of a clamp for fastening to the incus process are described separately in U.S. Pat. No. 5,935,167, U.S. Pat. No. 6,830,587 B2, and U.S. Pat. No. 7,628,812 B2, while U.S. 2008/0208338 A1 has proposed a specially embodied sling for mechanically coupling to another element of the human ossicular chain. In addition, DE 10 2009 016 468 B3, for example, has disclosed embodiments of the second fastening element in the form of a piston, a die, or a slotted bell. All of these known coupling elements, however, are not components of active hearing implants of the generic type in question here, but are instead components of passive ossicular chain prostheses of a different generic type and in addition, are in no position whatsoever to give any suggestion of the geometrical embodiment of the first coupling element according to the invention.

In addition to the postoperative position shifting described further above, another problem also arises after implantation of hearing implants: the middle ear of the human body represents a "semi-open storage medium." Each implant material that is introduced into the body as part of a reconstruction of the middle ear and its structures experiences a particular stress because a contaminated and infected environment prevails that generally corrodes the material. Since the goal of implanting a hearing implant must always be to achieve the longest possible, most complication-free dwell time of the implant in the middle ear of the patient, a long-term material corrosion can result in damage to the implant and/or can result in local infections. Both results are unacceptable. In order to lastingly prevent damage to the implant material and also to the surrounding tissue, in another particularly preferred embodiment of the invention, the surface of the device is completely or at least partially covered with a biologically active coating, in particular a coating with a growth-inhibiting and/or growth-promoting and/or antibacterial action.

A second fastening element that leads directly into the inner ear and is embodied for example in the form of a piston is provided, for example, with a growth-inhibiting coating in order to prevent an undesirable stiffening and resulting immobility.

In a particularly preferable embodiment of the device according to the invention, the mass distribution of the individual parts of the hearing implant is calculated as a function of a desired, preset or presettable frequency response of the sound conduction in the middle ear. Consequently, it is possible without significant additional technical complexity to achieve a certain degree of mechanical tuning of the sound propagation properties by means of an individually embodied hearing implant.

Such a tuning effect can be achieved in particular embodiments, for example in that at least one additional mass is fastened to the connecting element as a function of a desired, presettable frequency response of the sound conduction in the middle ear. In advantageous modifications of these embodiments, the additional mass is fastened by means of a clip to a part of the ossicular chain or the hearing implant. In addition, the additional mass and/or the clip can likewise be covered with a biologically active coating.

Additional features and advantages of the invention ensue from the claims and from the following detailed description of exemplary embodiments of the invention in conjunction with the figures in the drawings, which depict details that are essential to the invention. The individual features can each be implemented separately or can be united in any desired combination in variants of the invention.

The schematic drawings depict exemplary embodiments of the invention that will be described in greater detail in the description that follows.

DESCRIPTION OF THE PREFERRED EMBODIMENTS

Figure 1A:
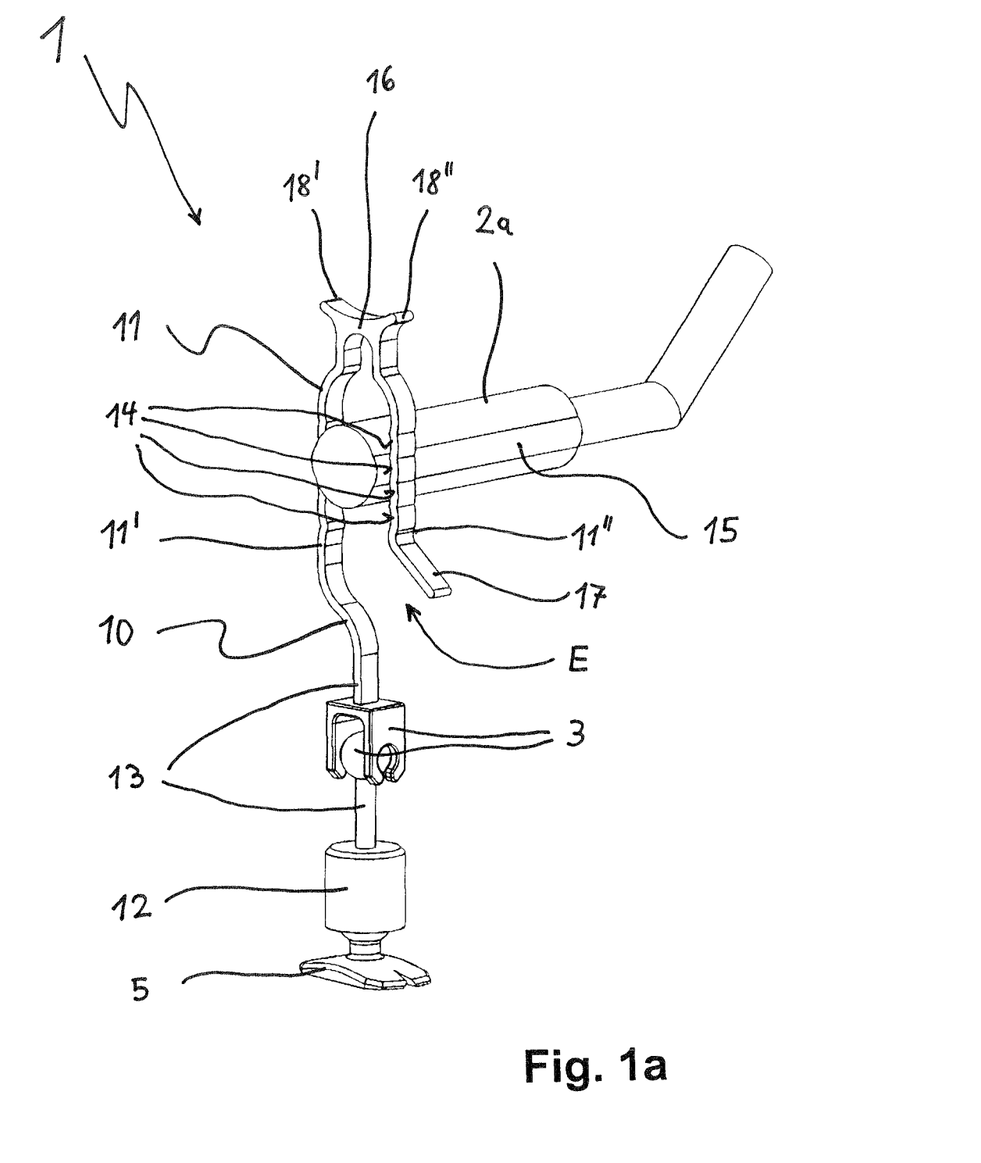
FIG. 1a is a three-dimensional schematic depiction of a flexible embodiment of the device according to the invention, having two parallel, axially extending protrusions on the actuator end piece, having a ball-and-socket joint in the shaft-shaped middle part, and having a receiving part for an Ω-shaped artificial stapes footplate as a second coupling element.
Figure 1B:
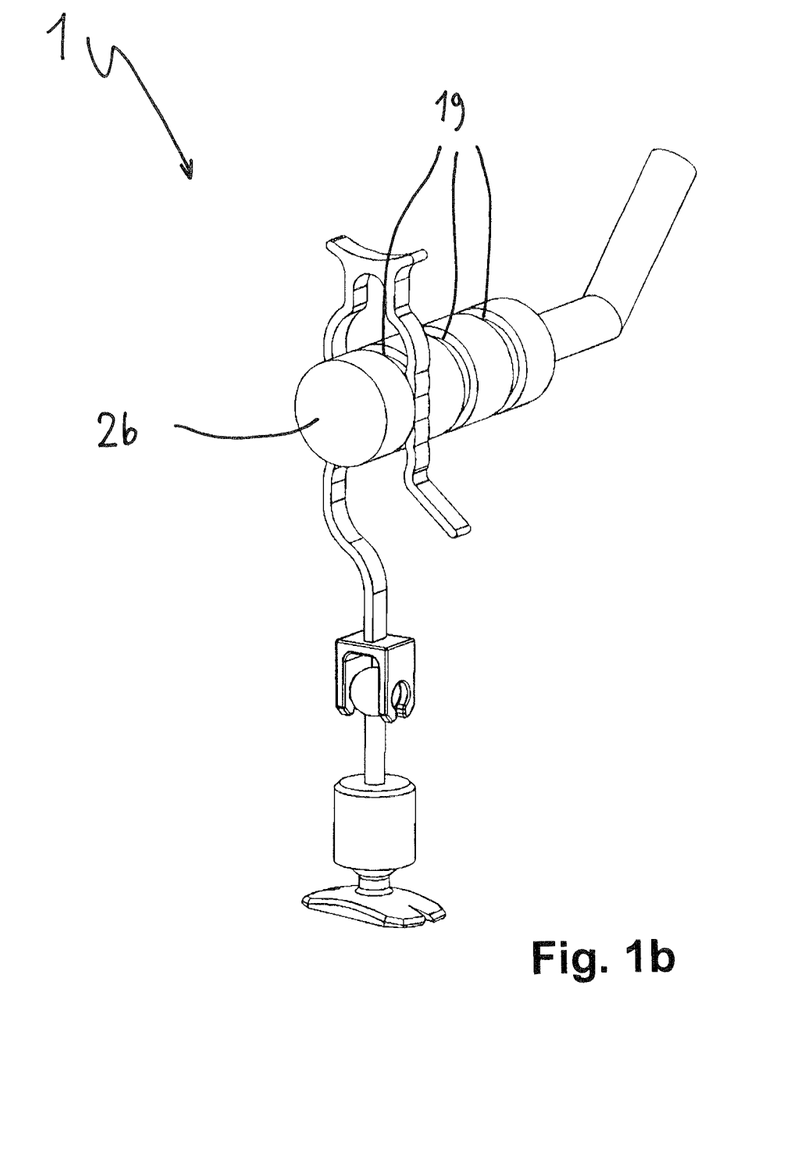
FIG. 1b shows an embodiment equivalent to the one in FIG. 1a, but with three parallel azimuthally extending annular grooves in the outer circumference of the actuator end piece.

The embodiments of the device 1 according to the invention, which are shown in three-dimensional schematic depictions in FIGS. 1a and 1b, serve to adjust and fix the relative position between an actuator end piece 2a; 2b of an active hearing implant on the one hand—not otherwise shown in detail in the drawings—and on the other hand, an element of the ossicular chain or a coupling part to the human inner ear, in particular to the perilymph of the labyrinth system or to the endolymphatic compartment.

Figure 2:
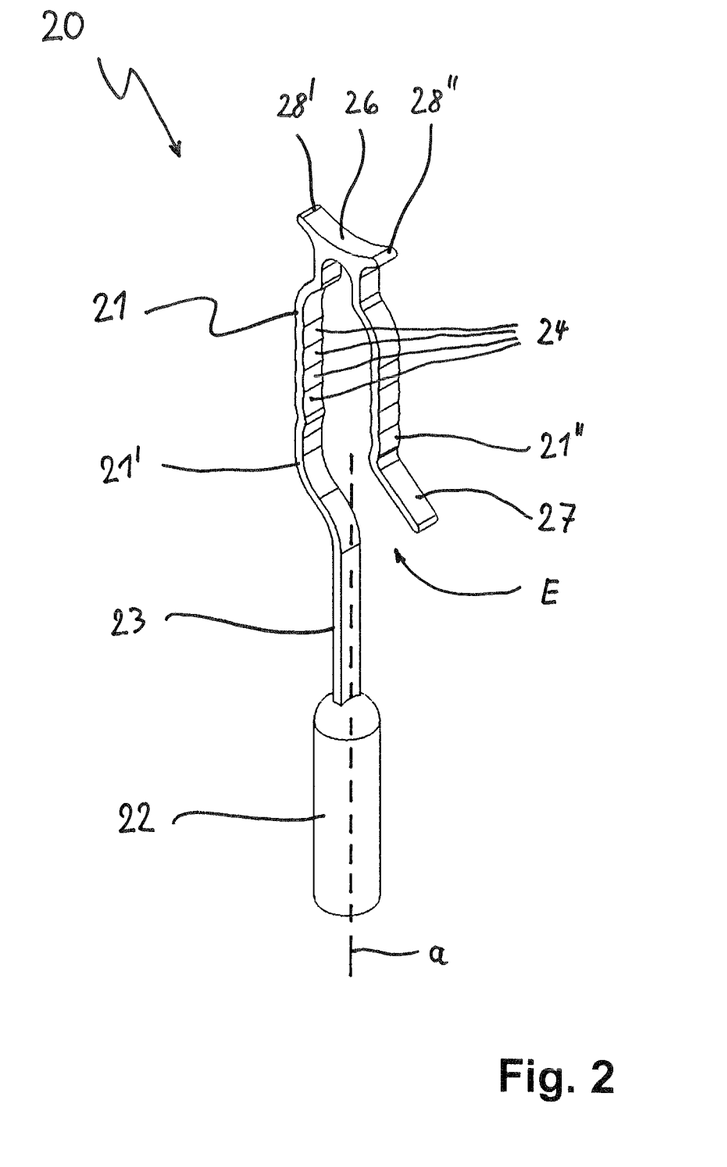
FIG. 2 is a three-dimensional schematic depiction of a simple embodiment of the connecting element according to the invention, with a continuous shaft-shaped middle part and a second coupling element embodied in the form of a piston.
Figure 3A:
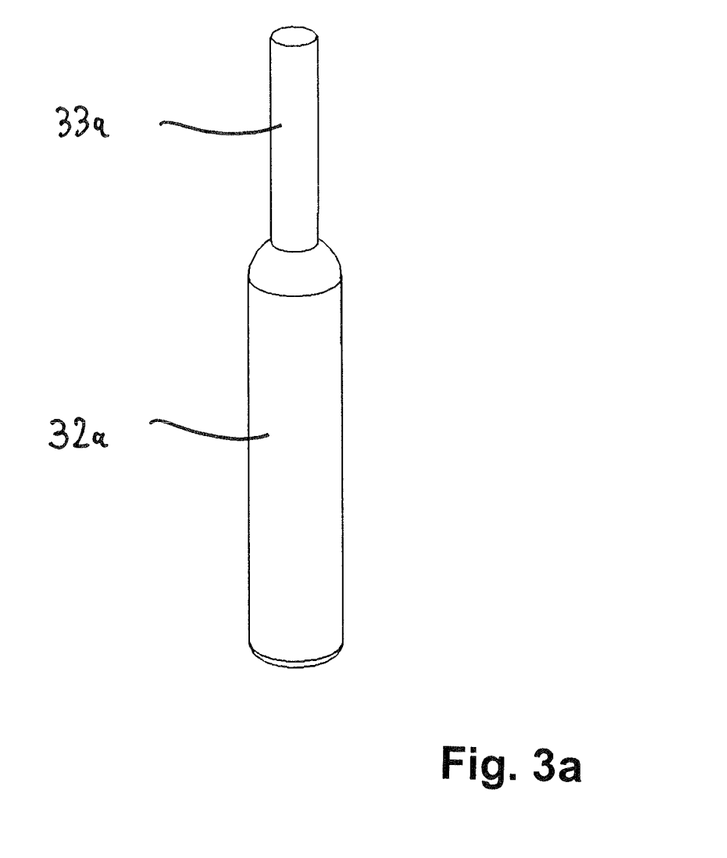
FIGS. 3a, b are schematic detail views of a second coupling element embodied in the form of a
  (a) piston
  (b) ball
  for directly coupling the connecting element to the inner ear.
Figure 3B:
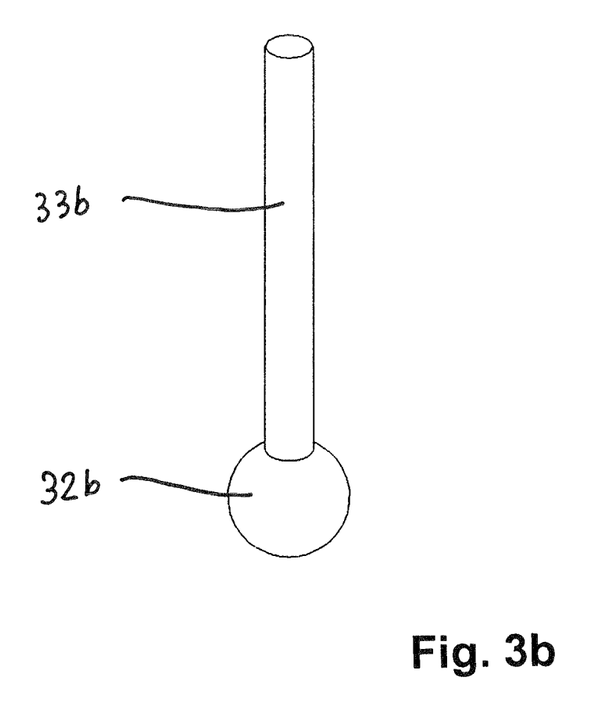
Figure 4A:
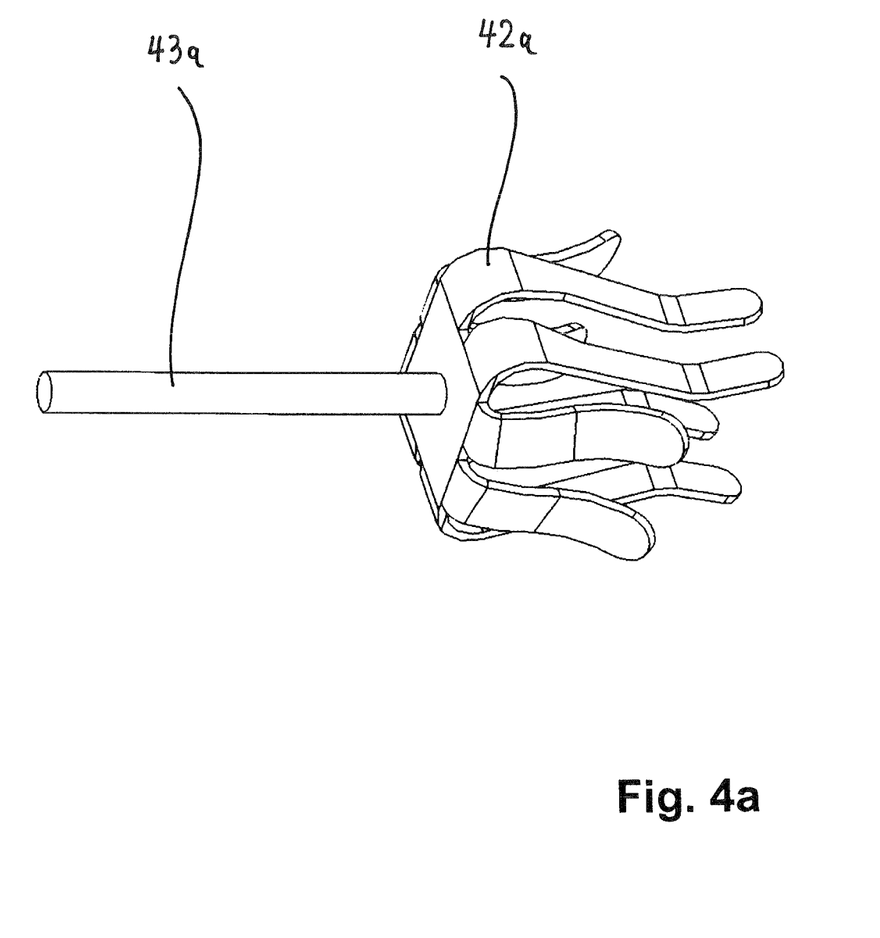
FIGS. 4a, b are schematic detail views of a second coupling element embodied in the form of a
  (a) clip
  (b) slotted bell
  for coupling the connecting element to the stapes head.
Figure 4B:
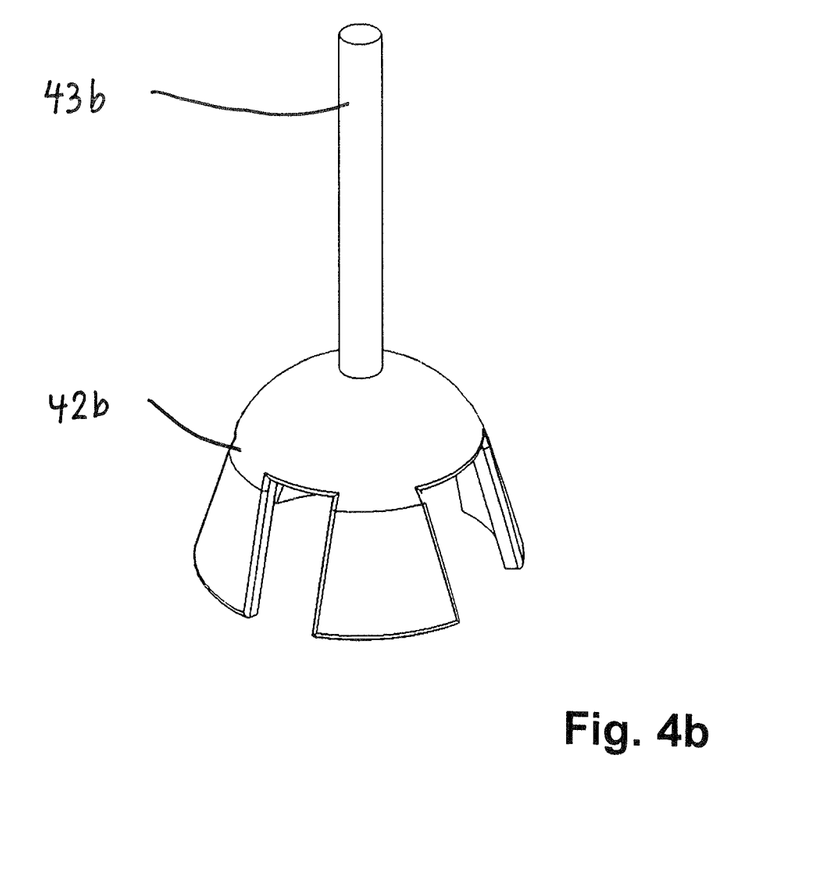
Figure 5:
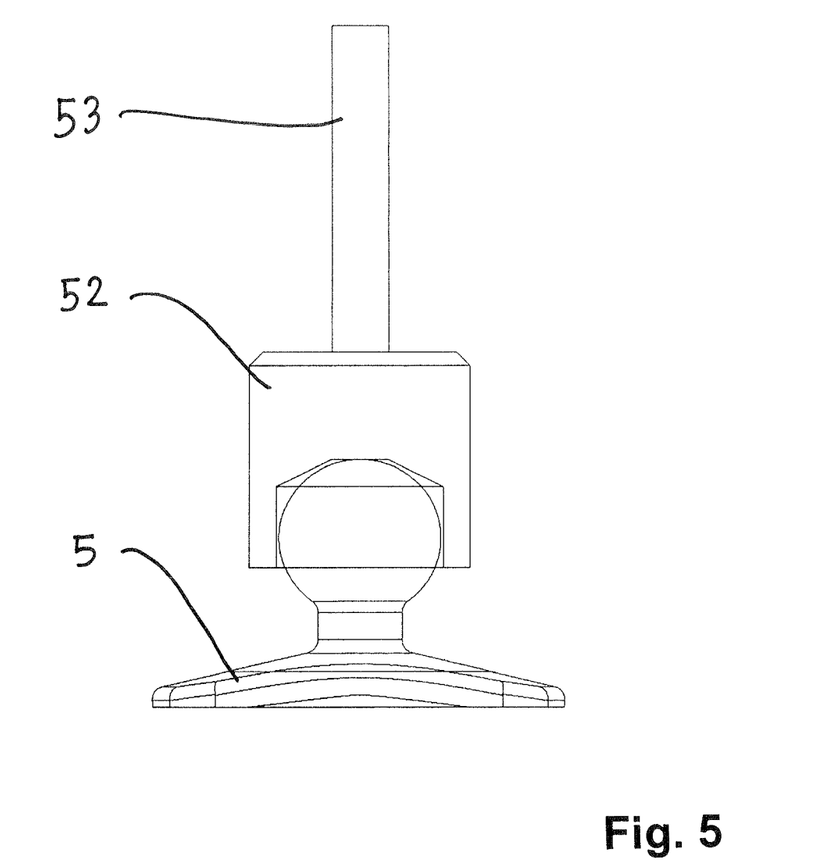
FIG. 5 is a schematic detail view of a second coupling element, which is embodied in the form of a receiving part for an Ω-shaped artificial stapes footplate and is for coupling the connecting element to the artificial stapes footplate.
Figure 6:
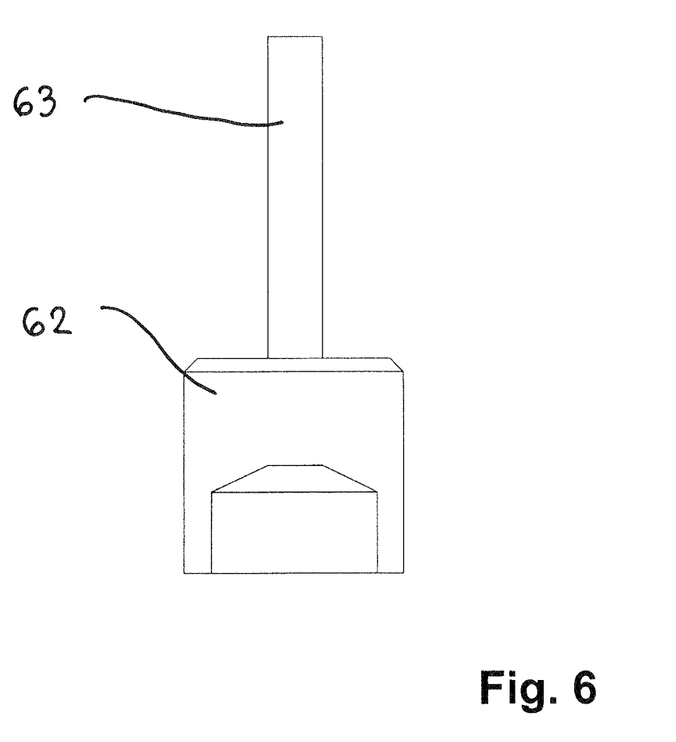
FIG. 6 is a schematic detail view of a second coupling element embodied in the form of a die for coupling the connecting element to the natural stapes footplate.
Figure 7:
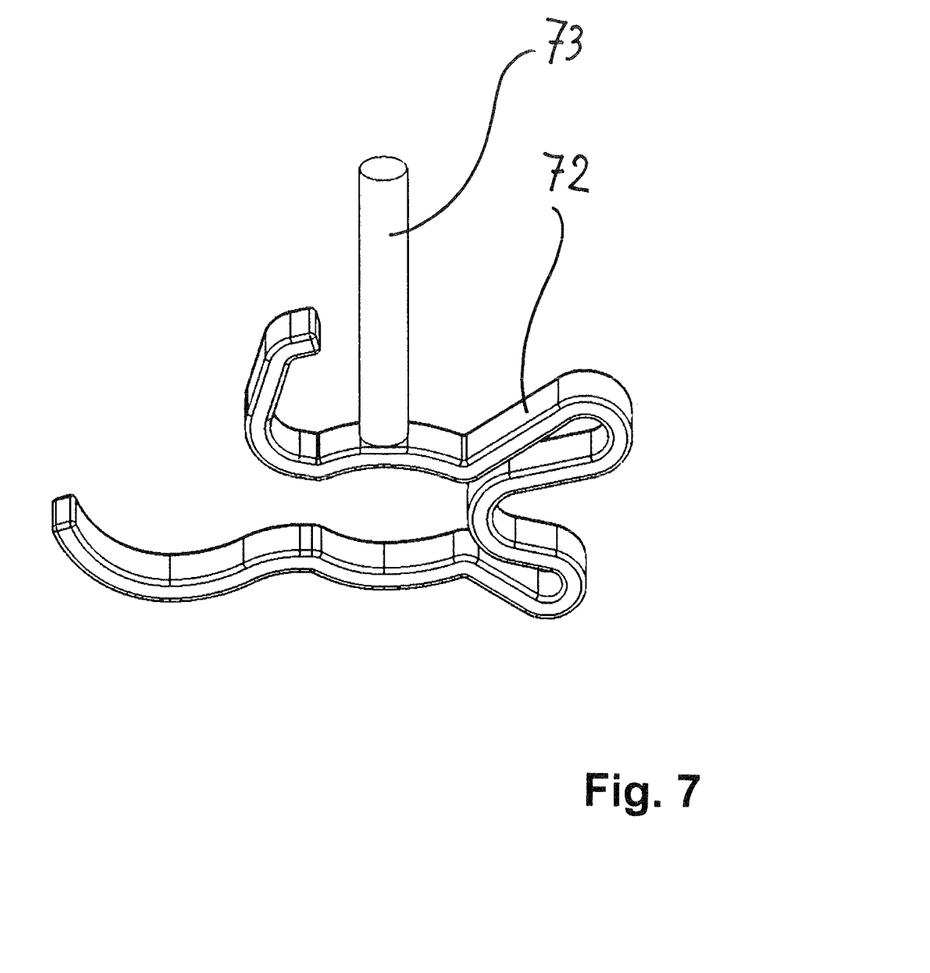
FIG. 7 is a schematic detail view of a second coupling element embodied in the form of a clamp for coupling the connecting element to the incus process.
Figure 8:
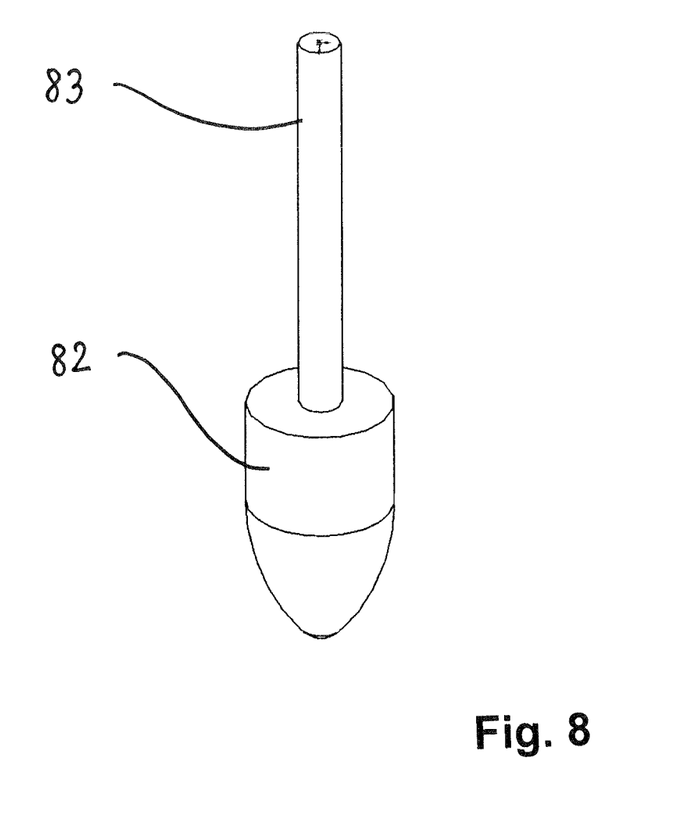
FIG. 8 is a schematic detail view of a second coupling element embodied in the form of a pin for coupling the connecting element to the incus body.

The device 1 is equipped with a connecting element 10; 20—also shown in another embodiment in FIG. 2—having a first coupling element 11; 21 for coupling the connecting element 10; 20 to the actuator end piece 2a; 2b, having a second coupling element 12; 22 for coupling the connecting element 10; 20 to the incus, the stapes, the stapes footplate, the oval window, or the round window of the human middle ear, and having a shaft-shaped middle part 13; 23 between the first coupling element 11; 21 and the second coupling element 12; 22.

Other embodiments of the second coupling element 32a; 32b; 42a; 42b; 52; 62; 72; 82 described in greater detail below are each schematically depicted with a shoulder of a shaft-shaped middle part 33a; 33b; 43a; 43b; 53; 63; 73; 83 in FIGS. 3a through 8.

According to the invention, the device 1 is distinguished by the fact that the first coupling element 11; 21 is geometrically embodied so that it encompasses the actuator end piece 2a with two opposing essentially parallel arms 11', 11"; 21', 21" and the two arms 11', 11"; 21' 21" each have a pattern element, which, in cooperation with the two arms 11', 11"; 21', 21", makes it possible to fix the encompassed actuator end piece 2a; 2b in selectable discrete axial positions in a direction parallel to the shaft axis a of the shaft-shaped middle part 13; 23; 33a; 33b; 43a; 43b; 53; 63; 73; 83.

In the embodiments shown in FIGS. 1a, 1b, and 2, the pattern elements of the arms 11', 11"; 21', 21" of the first coupling element 11; 21, on their inner surfaces, which rest against the outer circumference of the actuator end piece 2a; 2b in the implanted state, each have notches 14; 24 at the respective opposite axial positions of the two arms 11', 11"; 21', 21" for accommodating the actuator end piece 2a; 2b, which notches are situated spaced equidistantly apart from one another in the axial direction.

The actuator end piece 2a shown in FIG. 1a has elongated projections 15 on its outer circumference that are geometrically embodied so that they function as counterparts that fit the notches or indents 14; 24 at the discrete axial positions of the pattern elements of the first coupling element 11; 21.

By contrast, the actuator end piece 2b in FIG. 1b has azimuthally extending annular grooves 19 on its outer circumference that are geometrically embodied so that they function as counterparts that fit the notches or indents 14; 24 at the discrete axial positions of the pattern elements of the first coupling element 11; 21.

As is clearly visible in FIGS. 1a, 1b, and 2, the first arm 11'; 21' of the first coupling element 11; 21 transitions into the shaft-shaped middle part 13; 23 of the connecting element 10; 20, the second arm 11"; 21" is connected to the first arm 11'; 21' via a connecting piece 16; 26 so that the two arms are spaced laterally apart from each other, and at the end opposite from the connecting piece 16; 26, between the first arm 11'; 21' and the free end of the second arm 11"; 21, an insertion region E is provided for the insertion of the actuator end piece 2a; 2b. The free end of the second arm 11"; 21" transitions into an insertion facilitating element 17; 27 that extends diagonally outward in a direction oriented away from the first arm 11'; 21' and toward the outside of the second arm 11"; 21" in order to facilitate the insertion of the actuator end piece 2a; 2b into the insertion region E of the first coupling element 11; 21. The connecting piece 16; 26 can have two horns 18', 18"; 28', 28" that each protrude laterally outward in a direction oriented away from the shaft axis a of the shaft-shaped middle part 13; 23.

In the embodiments of the invention shown in FIGS. 1a and 1b, the connecting element 10 has a ball-and-socket joint 3 that is situated in the region of the shaft-shaped middle part 13. In lieu of the single ball-and-socket joint 3, it is also possible to use a ball-and-socket chain that would give the middle part 13 an even greater degree of flexibility.

The alternative embodiment shown in FIG. 2, however, features the fact that the connecting element 20 is embodied of one piece with the unit comprising the first coupling element 21, the shaft-shaped middle part 23, and the second coupling element 22.

Finally, FIGS. 3a through 8 show different embodiments of the second coupling element, namely in the form of a piston 22; 32a or ball 32b for coupling to the inner ear, in the form of a clip 42a or slotted bell 42b for coupling to the stapes head, in the form of a receiving part 12; 52 for accommodating an Ω-shaped artificial stapes footplate 5, in the form of a die 62 for coupling to the natural stapes footplate, in the form of a clamp 72 for coupling to the incus process, or in the form of a pin 82 for coupling to the incus body.

In embodiments of the invention not shown in detail in the drawings, an additional mass can be fastened to the connecting element 10; 20 as a function of a desired, presettable frequency response of the sound conduction in the middle ear.

Also not shown in the drawings are embodiments of the device 1 according to the invention in which at least some regions are provided with a biologically active coating, in particular a coating with a growth-inhibiting and/or growth-promoting and/or antibacterial action.

As a preferred material for the connecting element 10; 20 or parts thereof, at least in the region of the first coupling element 11; 21, a material with shape memory properties (=memory effect) is used, in particular a nickel/titanium alloy, preferably NITINOL.

It will be understood that each of the elements described above, or two or more together, may also find a useful application in other types of constructions differing from the types described above.

While the invention has been illustrated and described as embodied in a device for variable-length fixing of the actuator end piece of an active hearing implant in the middle ear, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for adjusting and fixing a relative position between an actuator end piece of an active hearing implant and an element of an ossicular chain or a coupling part to a human inner ear, the device comprising
    a connecting element having a first coupling element for coupling said connecting element to the actuator end piece,
    a second coupling element for coupling said connecting element to an incus, stapes, a stapes footplate, an oval window, or a round window of a human middle ear; and
    a shaft-shaped middle part between said first coupling element and said second coupling element, said shaft-shaped middle part defining a shaft axis,
    wherein said first coupling element is geometrically configured so as to encompass the actuator end piece with two opposing parallel arms,
    wherein said two arms each have a pattern element, which in cooperation with said two arms fixes the encompassed actuator end piece in selectable discrete axial positions in a direction parallel to said shaft axis of said shaft-shaped middle part, and
    wherein each of said pattern elements is configured with formations selected from the group consisting of notches and indents at the respective opposite axial positions of said two arms for accommodating the actuator end piece.

2. The device as defined in claim 1, wherein said pattern elements of said arms of said first coupling element are provided on inner surfaces, which rest against an outer circumference of the actuator end piece in an implanted state.

3. The device as recited in claim 1, wherein said pattern elements are on said inner surfaces of said two arms and are situated spaced equidistantly apart from one another in the axial direction.

4. The device as recited in claim 1, wherein said pattern elements selected from the group consisting of said notches and said indents are geometrically configured so that they function as counterparts to projections on an outer circumference of the actuator end piece at discrete axial positions of said pattern elements of said first coupling element.

5. The device as defined in claim 1, wherein said pattern elements are selected from the group consisting of said notches and said indents are configured so that they function as counterparts to azimuthally extending annular grooves on an outer circumference of the actuator end piece at discrete axial positions of said patterns element of said first coupling element.

6. The device as defined in claim 1, wherein said arms have a first arm which transitions into said shaft-shaped middle part of said connecting element, and a second arm which is connected to said first arm via a connecting piece, so that said two arms are spaced laterally apart from each other, and at an end opposite from said connecting piece, between said first arm and a free end of said second arm, an insertion region is provided for insertion of the actuator end piece.

7. The device as defined in claim 6, wherein said free end of said second arm transitions into an insertion facilitating element that extends diagonally outward in a direction oriented away from said first arm and toward an outside of said second arm to facilitate the insertion of the actuator end piece into the insertion region of said first coupling element.

8. The device as defined in claim 6, wherein said connecting piece is situated at a free end of said first coupling element oriented away from said shaft-shaped middle part.

9. The device as defined in claim 6, wherein said connecting piece has two horns that each protrude laterally outward in a direction oriented away from said shaft axis of said shaft-shaped middle part.

10. The device as defined in claim 1, wherein said connecting element has a member selected from the group consisting of a ball-and-socket joint and a ball-and-socket chain that is partially situated in a region of said shaft-shaped middle part.

11. The device as defined in claim 1, wherein said first coupling element and said shaft-shaped middle part of the connecting element are of one piece with each other.

12. The device as defined in claim 11, wherein said connecting element is one piece with a unit comprising said first coupling element, said shaft-shaped middle part, and said second coupling element.

13. The device as defined in claim 1, wherein said connecting element is composed, entirely or partially, at least in a region of said coupling element, of material with shape memory properties.

14. The device as defined in claim 13, wherein said connecting element in said region of said first coupling element is composed of nickel/titanium alloy.

15. The device as defined in claim 14, wherein said nickel/titanium alloy is a NITINOL.

16. The device as defined in claim 1, wherein said second coupling element is formed as an element selected from the group consisting of a piston or a ball for coupling to the inner ear, a clip or slotted bell for coupling to a stapes head, a receiving part for accommodating an artificial stapes footplate, a die for coupling to the natural stapes footplate, a clamp for coupling to an incus process, and a pin for coupling to an incus body.

17. The device as defined in claim 1, further comprising a biologically active coating provided in at least some regions of the device.

18. The device as defined in claim 17, wherein said coating is a coating selected from the group consisting of a growth-inhibiting coating, a growth-promoting coating, an anti-bacterial action coating, and combinations thereof.

* * * * *